(12) United States Patent
Nelissen (10) Patent No.: US 7,832,402 B2
(45) Date of Patent: Nov. 16, 2010

(54) DEVICE FOR TREATING NIGHTTIME BREATHING PROBLEMS

(76) Inventor: Jozef Frans Nelissen, Elsendonkstraat 142, BE-2560, Nijlen (BE)

( * ) Notice: Subject to any disclaimer, the term of this patent is extended or adjusted under 35 U.S.C. 154(b) by 771 days.

(21) Appl. No.: 10/567,372

(22) PCT Filed: Aug. 4, 2004

(86) PCT No.: PCT/BE2004/000112

§ 371 (c)(1),
(2), (4) Date: Apr. 13, 2007

(87) PCT Pub. No.: WO2005/013867

PCT Pub. Date: Feb. 17, 2005

(65) Prior Publication Data

US 2008/0135056 A1   Jun. 12, 2008

(30) Foreign Application Priority Data

Aug. 8, 2003   (BE) ................................ 2003/0441

(51) Int. Cl.
*A61F 5/56* (2006.01)
*A61C 3/00* (2006.01)
(52) U.S. Cl. .......................................... 128/848; 433/6
(58) Field of Classification Search ................. 128/848, 128/859, 860, 861, 862, 857; 433/6, 7, 18, 433/19, 24
See application file for complete search history.

(56) References Cited

U.S. PATENT DOCUMENTS

| 3,854,208 | A | | 12/1974 | Arant |
| 4,901,737 | A | * | 2/1990 | Toone .......................... 128/848 |
| 5,281,133 | A | | 1/1994 | Farzin-Nia |
| 5,409,017 | A | * | 4/1995 | Lowe .......................... 128/848 |
| 5,868,138 | A | * | 2/1999 | Halstrom ..................... 128/848 |
| 6,729,335 | B1 | | 5/2004 | Halstrom |
| 6,769,910 | B1 | | 8/2004 | Pantino |

FOREIGN PATENT DOCUMENTS

EP   1247498 A   10/2002

\* cited by examiner

*Primary Examiner*—Patricia M Bianco
*Assistant Examiner*—Ophelia Hawthorne
(74) *Attorney, Agent, or Firm*—Harness, Dickey & Pierce, P.L.C.

(57) ABSTRACT

A device for treating breathing problems is disclosed, including a shaped part fitting onto the teeth of the lower jaw, a shaped part fitting onto the teeth of the upper jaw, and at least one adjustable connecting device between the upper and lower shaped part for forward/backward and upward/downward adjustment of the upper shaped part relative to the lower shaped part. One of the shaped parts is provided at the front with a slide mechanism including a slide element which is slidable laterally to a limited extent along a guide element. Further, the adjustable connecting devices are fixedly connected to the other shaped part on one side and to the slide element on the other, thus allowing a precise forward/backward and upward/downward adjustment with a limited freedom of movement of the lower jaw in relation to the upper jaw.

15 Claims, 6 Drawing Sheets

DEVICE FOR TREATING NIGHTTIME BREATHING PROBLEMS

CROSS REFERENCE TO RELATED APPLICATIONS

This application claims priority under 35 USC §119 from Belgium patent application no. 2003/0441 filed Aug. 8, 2003, the contents of which are incorporated by reference in its entirety.

BACKGROUND OF THE INVENTION

The invention relates to a device for treating breathing problems, in particular to an oral apparatus, comprising a shaped part fitting onto the teeth of the lower jaw, a shaped part fitting onto the teeth of the upper jaw, and adjustable connecting means between the upper and lower shaped part for forward/backward and upward/downward adjustment of the upper shaped part relative to the lower shaped part.

DESCRIPTION OF RELATED ART

Nighttime breathing problems, which can for instance result in snoring, sleep apnoea syndrome or other sleep disorders, are a generally known problem. When a person sleeps, the rear part of the tongue may tend to slide backwards and so wholly or partially close off the pharyngeal airway. It is known to solve such breathing problems with a device which can be placed in the mouth and with which the lower jaw is placed further forward in relation to the upper jaw. The neck muscles are hereby forced into a tensioned position, whereby the tongue moves forward and the airway is left clear.

The said devices placeable in the mouth are generally known and can be found in a number of different embodiments. According to a possible embodiment, an adjustable hook is used which is connected by means of a forward/backward adjustable screw to the upper shaped part and can be coupled to the lower shaped part. Such a hook has the drawback that it still allows a certain upward/downward movement, which causes an inaccuracy in the vertical (upward/downward) adjustment. Such a hook is furthermore irritating for the tongue and can come loose during sleep.

The invention has for its object to provide a device according to the preamble of claim 1 which is more user-friendly, in particular is more agreeable to wear, and allows a precise forward/backward and upward/downward adjustment with a limited freedom of movement of the lower jaw in relation to the upper jaw.

BRIEF SUMMARY OF THE INVENTION

The device according to the preamble of claim 1 is distinguished for this purpose in that one of the shaped parts is provided at the front with a slide mechanism consisting of a slide element which is slidable laterally to a limited extent along a guide element, and that the adjustable connecting means are fixedly connected to the other shaped part on one side and to the slide element on the other.

By arranging a slide mechanism between the adjustable connecting means and one of the shaped parts a limited lateral movement of the lower shaped part relative to the upper shaped part is made possible. This slide mechanism operates independently of the adjustable connecting means and thus allows a precise upward/downward and forward/backward adjustment, without this adjustment being impeded by the slide mechanism. By arranging the slide mechanism on the front of the shaped part, for instance as closely as possible to the rear side of the front teeth in the position placed in the mouth, there is more space for the tongue and the movement of the tongue is impeded as little as possible.

The term "shaped part" must be interpreted broadly here, and is understood to mean for instance a brace with a palate plate as well as a flexible bite-block.

According to a preferred embodiment the dimensions of the guide element and the slide element are closely-sized transversely of the guiding direction. The slide element is hereby substantially immobile in the plane perpendicularly of the guiding direction, and the vertical (upward/downward) adjustment is not affected by the lateral freedom of movement provided by the slide mechanism.

According to a possible variant, the guide element is a rod mounted between two points of the one shaped part, and the slide element is a hollow tube slidable around this rod. In such a variant the length of the hollow tube can be chosen as a function of the desired maximum lateral displacement. Many other variants of the slide mechanism are of course also possible which likewise fall within the scope of the invention, and some examples of which are given in the figure description.

The slide element can preferably be snapped onto the guide element. These so-called Asnap-on® slide elements have the advantage that the shaped parts can each be placed separately in the mouth, whereafter the slide element is snapped onto the guide element.

The adjustable connecting means preferably comprise a substantially vertical adjusting screw with double screw thread for upward/downward adjustment of the upper shaped part relative to the lower shaped part, which adjusting screw co-acts on one outer end with a first threaded bore connected via a connecting piece to the slide element, and which co-acts on its other outer end with a second threaded bore provided on the front side of the other shaped part, wherein a rotation of the adjusting screw changes the distance between the lower and upper threaded bores.

According to a possible embodiment, the vertical adjusting screw is provided substantially in the middle with an encircling flange with radially directed openings in which a rod fits for the purpose of turning the adjusting screw through rotation of the rod. In this manner the vertical distance can be easily adjusted while the device is being placed in the mouth. Such adjusting screws with double screw thread are already used in orthodontics, and in particular in braces for widening the upper or lower jaw, wherein the screw is built in between two parts of a palate plate.

In order to obtain a stable vertical adjustment, the vertical adjusting screw is preferably enclosed on both sides by telescopically acting tubes.

According to a further developed embodiment of the invention, the connecting piece is provided with a horizontal adjusting screw for forward/backward adjustment of the one shaped part relative to the other, which horizontal adjusting screw co-acts on one outer end with a threaded passage mounted on the slide element. The horizontal adjusting screw is preferably provided on its other outer end with a screw head, and the connecting piece is provided with a horizontally oriented hole through which the horizontal adjusting screw extends.

In the preferred embodiment the adjustable connecting means are at least partially received in a housing which is rounded on the outside such that the device feels soft in the mouth of the patient.

BRIEF DESCRIPTION OF THE DRAWINGS

The device will be further elucidated with reference to the annexed drawings and the associated figure description of a non-limitative embodiment of the device according to the invention. In the drawing.

DETAILED DESCRIPTION OF THE INVENTION

Figure 1:
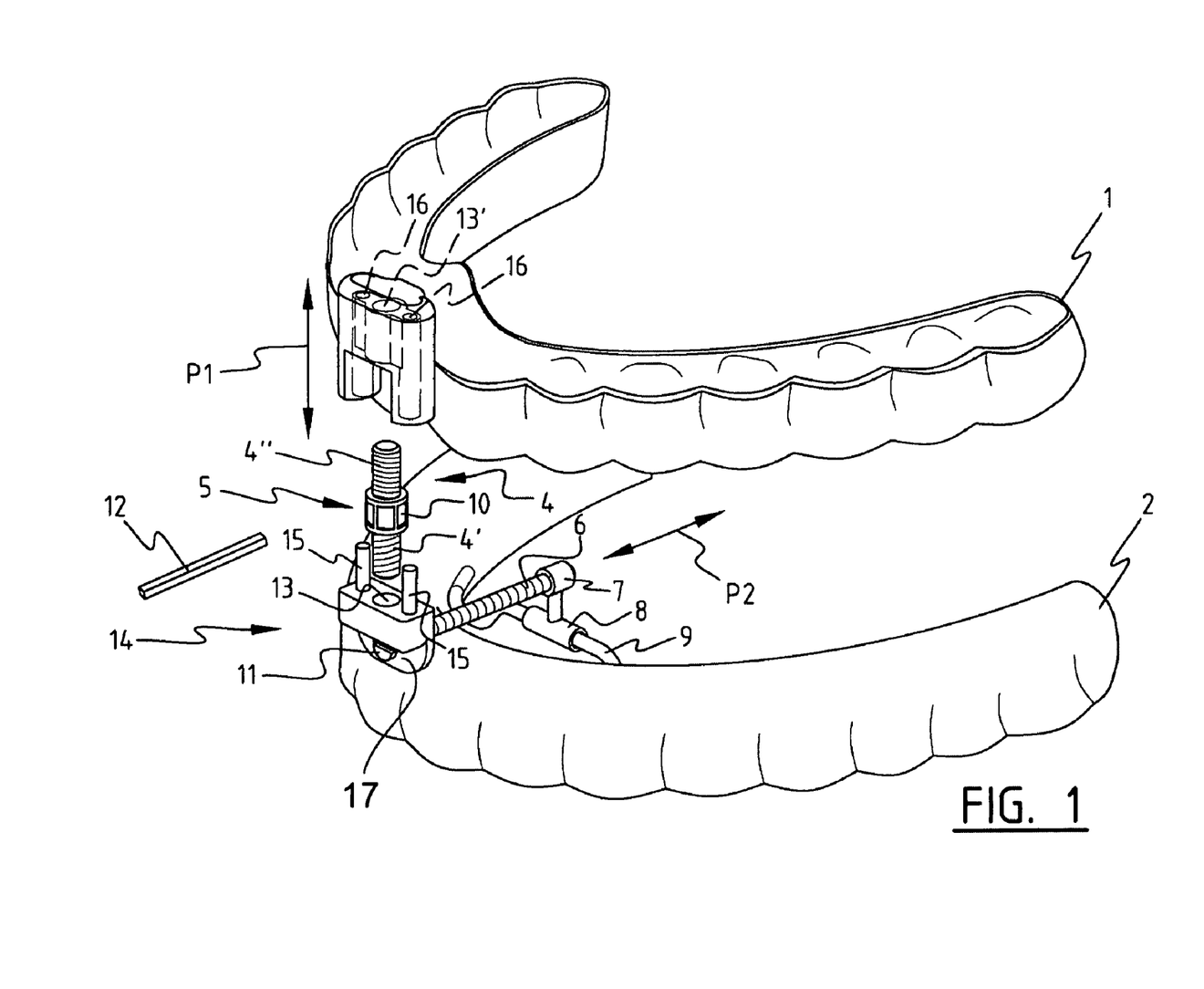
FIG. 1 is a perspective view of a possible embodiment of the device according to the invention.
Figure 2:
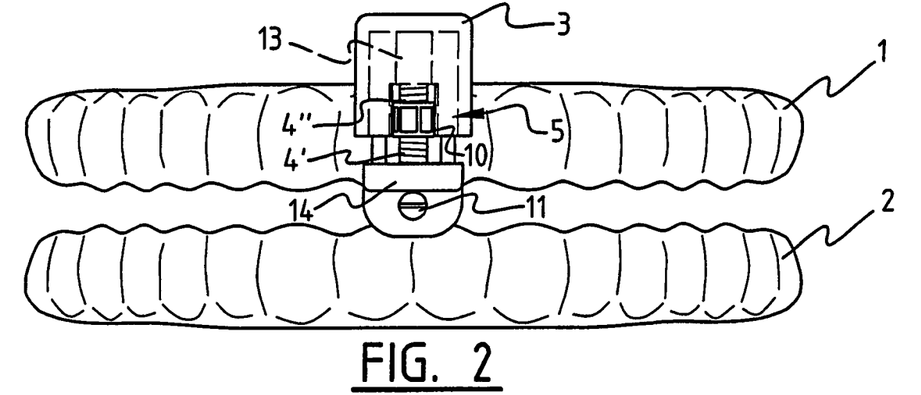
FIG. 2 is a front view of the embodiment of FIG. 1.
Figure 3:
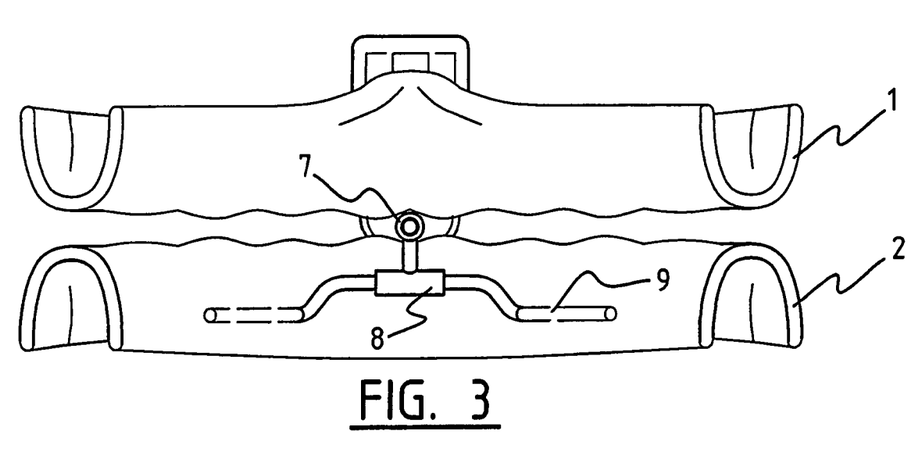
FIG. 3 is a rear view of the embodiment of FIG. 1.
Figure 4:
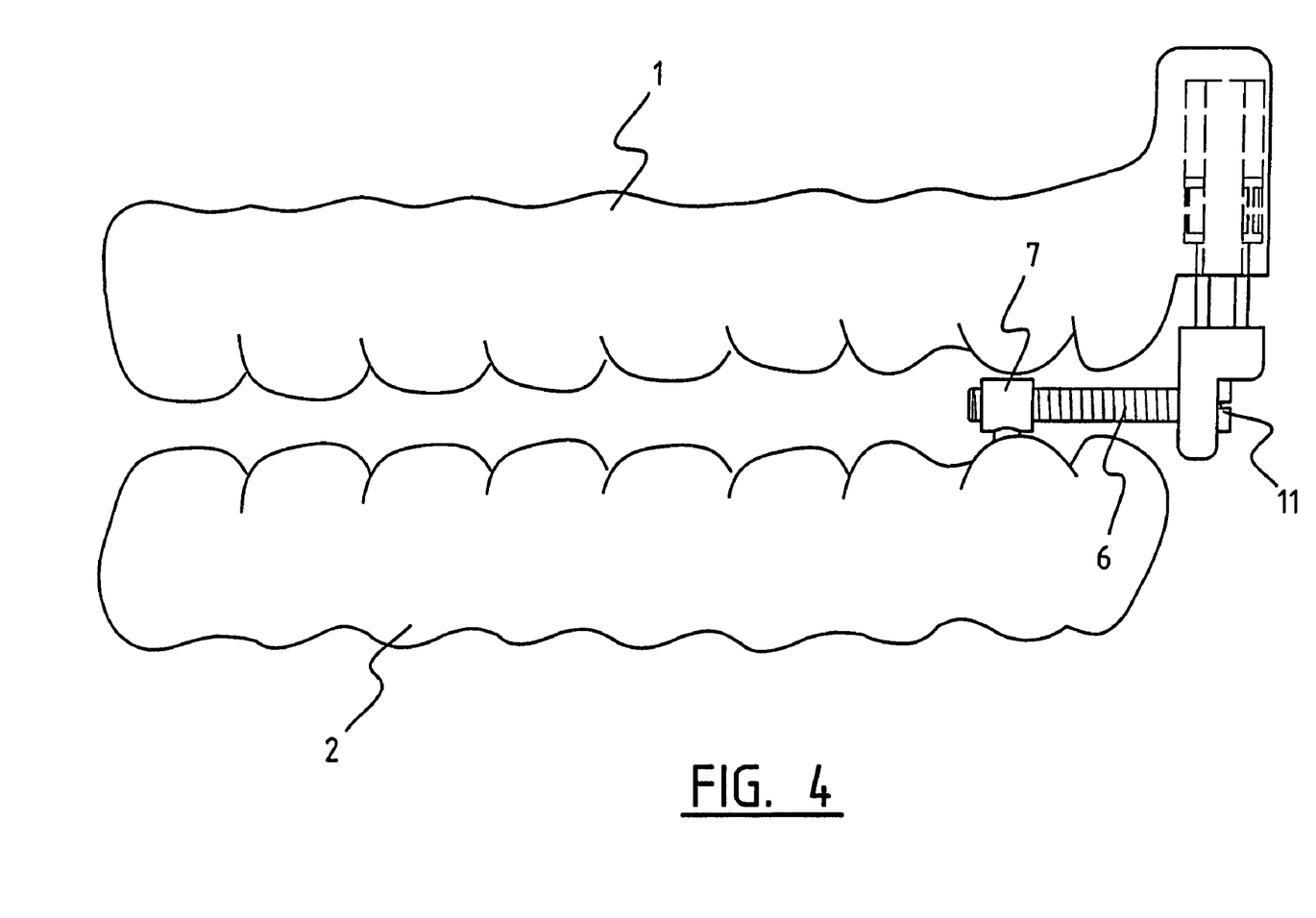
FIG. 4 is a side view of the embodiment of FIG. 1.

The embodiment shown in FIG. 1 comprises a shaped part 2 fitting onto the teeth of the lower jaw, referred to hereafter as lower shaped part, and a shaped part 1 fitting onto the teeth of the upper jaw, referred to hereafter as upper shaped part. Note that these shaped parts can for instance also take the form of braces with a metal arch and palate plate.

The adjustable connecting means for forward/backward adjustment, as indicated with arrow P2, and for upward/downward adjustment, as indicated with arrow P1, of the upper shaped part relative to the lower will now be elucidated.

The adjustable connecting means comprise a substantially vertical adjusting screw 4 with double screw thread for upward/downward adjustment (P1). Adjusting screw 4 is provided substantially in the middle with an encircling flange 5 with radially directed openings 10 into which a rod 12 fits. This adjusting screw 4 is rotated at one end in a first threaded bore 13 and at its other end in a second threaded bore 13' provided on the upper shaped part 1. By rotating the rod 12 the screw 4 is rotated deeper into threaded bores 13, 13' such that the distance between the lower and upper threaded bores 13, 13', and therefore also the distance between upper and lower shaped parts, changes. A rotation of the screw through a quarter-turn corresponds for instance to a difference in distance of 0.2 mm. In this manner the vertical distance between upper and lower shaped part can thus be adjusted precisely.

In order to impart additional strength to the vertical adjusting screw 4, it is enclosed on either side by telescopically acting tubes 15, 16. A spring can optionally be arranged in each hollow tube 16, which spring supports against the solid tube 15.

Threaded bore 13 is included in a connecting piece 14 which is provided with a downward directed flange 17 which is substantially parallel to the front side of the shaped parts and in which a hole is arranged. Through this hole extends a horizontal adjusting screw 6 for forward/backward (P2) adjustment of the shaped parts. This horizontal adjusting screw 6 co-acts with a threaded passage 7 mounted on a slide element 8. By tightening the screw 6 it will extend further through threaded passage 7, whereby the lower shaped part 2 is pulled forward. Note that the horizontal adjusting screw 6 extends loosely through the hole in flange 17 such that it is always possible to move the lower jaw further forward than is adjusted. This movement further forward tensions the throat muscles more on the one hand, while creating a certain freedom of movement on the other, whereby the device is more joint-friendly.

The lower shaped part 2 is provided at the front with a slide mechanism which consists of a slide element 8 slidable laterally to a limited extent along a guide element 9. Guide element 9 is here a rod fixed between two points on the lower shaped part, and the slide element 8 is a hollow tube slidable around this rod. The dimensions of guide element 9 and slide element 8 are closely-sized transversely of the guiding direction, i.e. the slide element is substantially immobile in the direction perpendicular to the guiding direction. The length of hollow tube 8 can be chosen as a function of the desired maximum lateral displacement. In the case of a patient who has many problems with his/her joints it is possible for instance to opt for a relatively short tube 8 and a relatively long guide element 9 such that the lateral freedom of movement is increased.

Figure 5A:
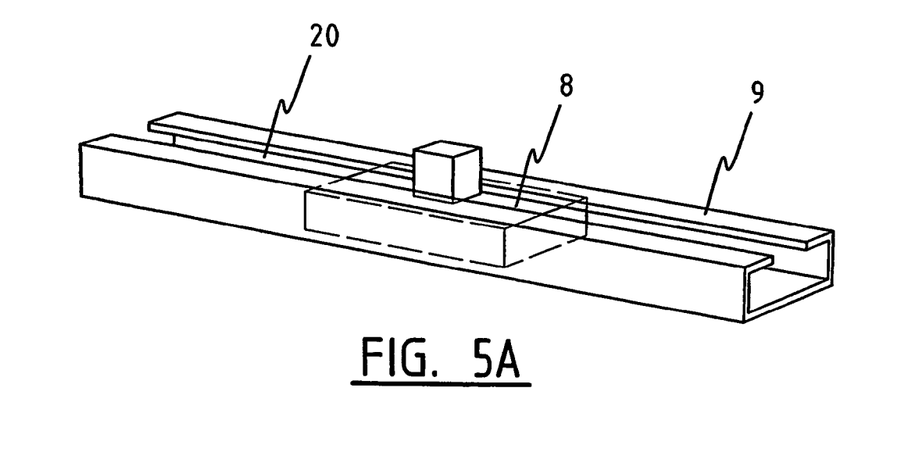
FIGS. 5A, B show a number of embodiment variants of the slide mechanism of the device according to the invention.
Figure 5B:
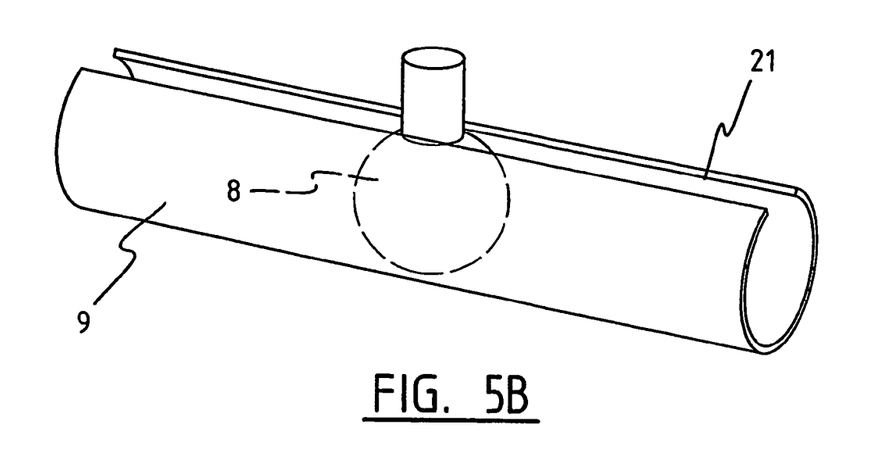

It should be understood that the slide mechanism can be embodied in many other ways; some possible embodiment variants are shown in FIGS. 5A and B.

According to the variant of FIG. 5A, a block-shaped slide element is used which is guided in a hollow tube provided on the top with a slot 20. FIG. 5B shows another variant wherein the guide element consists of a cylindrical tube provided on the top with a slot 21. Slide element 8 here takes a spherical form so that, in addition to the sliding movement, a limited swinging movement is also possible in the plane perpendicularly of slot 2 and parallel to the guiding direction.

The adjustable connecting means are fixedly connected to upper shaped part 2 on one side and to slide element 8 on the other. So as to make wearing of the device as pleasant as possible, it is recommended that the adjustable connecting means are at least partially received in a housing which is rounded on the outside.

Figure 6:
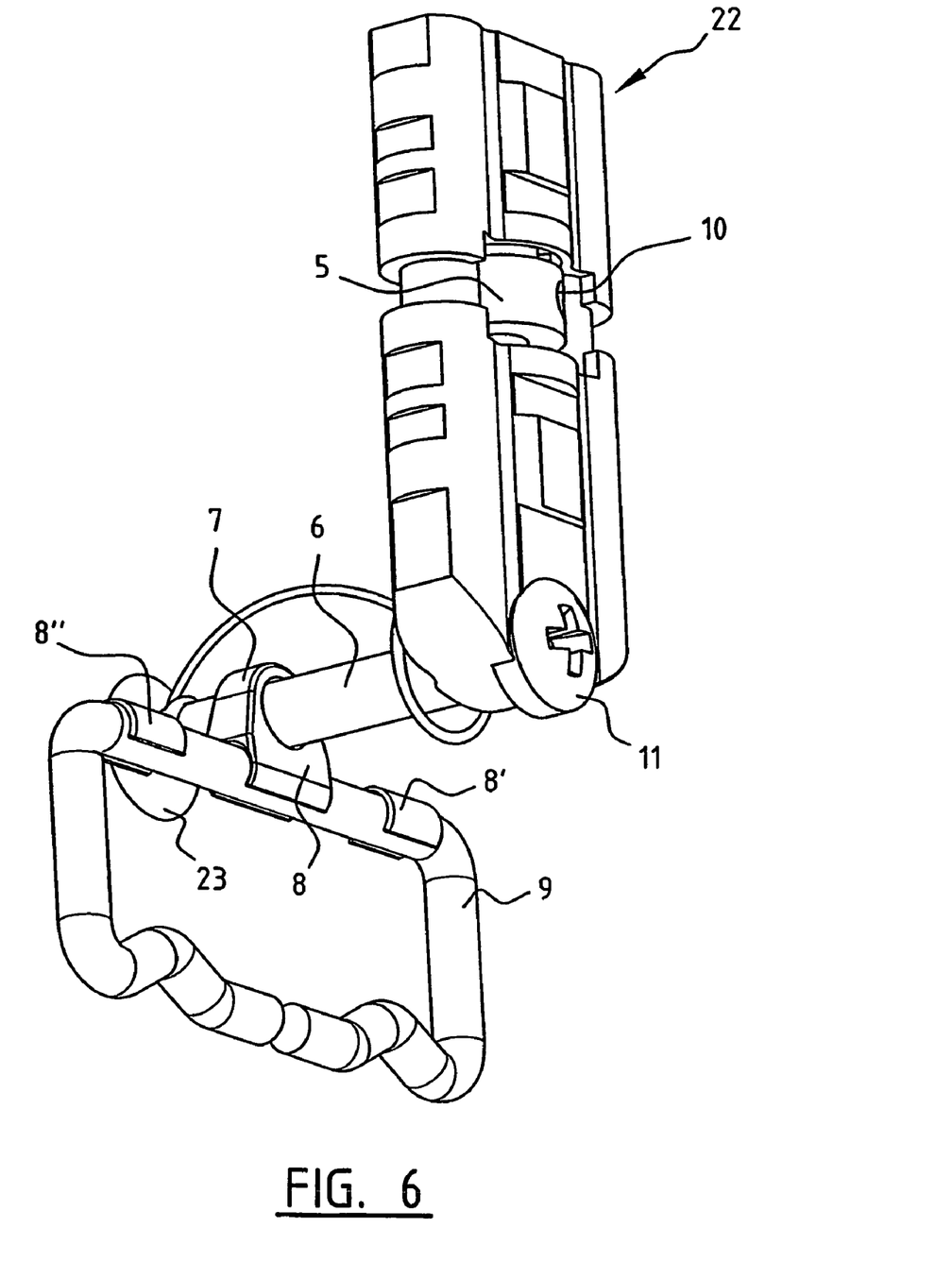
FIG. 6 is a perspective view of a second embodiment of the device according to the invention.

FIG. 6 shows a second embodiment variant of the device according to the invention. Guide element 9 is provided here with two extra hollow tubes 8', 8", whereby the lateral movement of the slide element is limited further. These hollow tubes 8, 8', 8" can all be embodied as snap-on elements which can be snapped easily onto the guide element.

As can be seen in FIGS. 1 and 6, the threaded bores and the vertical adjusting screw are enclosed by a housing which is rounded on the outside. In the variant of FIG. 6 the horizontal adjusting screw 6 is provided at the rear with a soft top 23, and threaded bore 7 and slide element 8 are embodied integrally without sharp edges.

The skilled person will readily appreciate that this housing can be further refined. Particularly the horizontal adjusting screw 6 with threaded bore 7 could for instance likewise be provided with a housing having a smooth feel.

Figure 7:
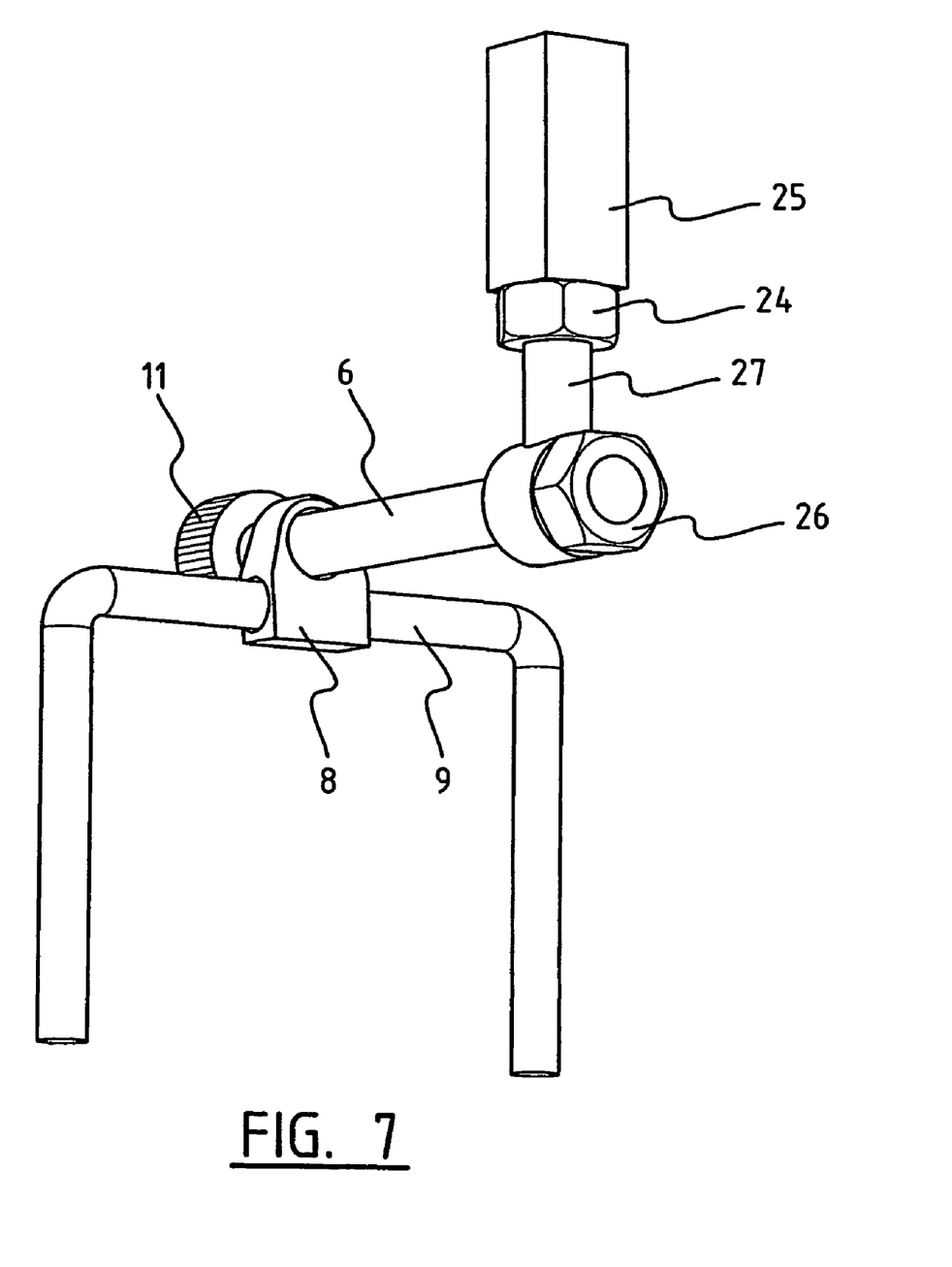
FIG. 7 is a perspective view of a third embodiment of the device according to the invention.

FIG. 7 shows a third embodiment variant of the device according to the invention. The slide element is here provided with a passage through which extends the guide element 9. In the third embodiment the horizontal adjusting screw 6 is placed the other way around, with its head 11 at the rear side, and a counter nut 27 is mounted on the end of the screw 6 (at the front side). To adjust the horizontal adjusting screw 6, the device has to be taken out of the mouth whereupon the position of the horizontal adjusting screw 6 can be adjusted with a screwdriver. The adjustable connecting means 22 for the upward/downward adjustment of the upper shaped part relative to the lower shaped part are even more compact in the third embodiment and are partially provided with a soft envelope. Said connecting means for the upward/downward adjustment can be partially built in the upper shaped part, so that the discomfort for the user is minimal. The adjustment connecting means comprise a vertical screw thread 27, a nut 24 fitting thereon, and a housing 25 provided with a threaded bore (not shown) co-acting with the screw thread 27. For the upward/downward adjustment the shaped parts between which the connecting means are acting, need to be taken out of the mouth and turned relative to each other around the axis of the screw thread 27, whereby the screw thread extends more or less deep in the threaded bore, i.e. in the housing. In that way the vertical distance between the upper and lower shaped part can be adjusted precisely with a very compact construction. Further there is provided a counter nut 24 which is screwed up to the housing and fixes the whole.

The scope of protection of the invention is not limited to the above illustrated embodiments, but is defined by the following claims.

The invention claimed is:

1. Device for treating breathing problems, comprising:
a lower shaped part fitting onto the teeth of the lower jaw,
an upper shaped part fitting onto the teeth of the upper jaw, and
at least one adjustable connecting means between the upper and lower shaped part for forward/backward and upward/downward adjustment of the upper shaped part relative to the lower shaped part,
wherein,
one shaped part of said upper and lower shaped parts is provided at the front with a slide mechanism including a slide element which is slidable laterally to a limited extent along a guide element,
the at least one adjustable connecting means has a first end and a second end, said first end being fixedly connected to the front side of the other shaped part of said upper and lower shaped parts, such that said first end is in front of the teeth when said other shaped part is placed in the mouth, and said second end being connected to the slide element;
the at least one adjustable connection means includes
a horizontal adjusting screw for forward/backward adjustment of said one shaped part relative to said other shaped part,
a vertical adjusting screw for the upward/downward adjustment of said one shaped part relative to said other shaped part, and
a coupling piece for coupling said horizontal adjusting screw with said vertical adjusting screw.

2. Device as claimed in claim 1, wherein said vertical adjusting screw has a first and a second outer end, and is provided with double screw thread for upward/downward adjustment of the upper shaped part relative to the lower shaped part, which vertical adjusting screw co-acts at its first outer end with a first threaded bore in the coupling piece, and which co-acts on its second outer end with a second threaded bore provided on the front side of the other shaped part, wherein a rotation of the adjusting screw changes the distance between the lower and upper threaded bores.

3. Device as claimed in claim 2, wherein the vertical adjusting screw is provided with an encircling flange substantially in the middle between its first and second outer end, said encircling flange having radially directed openings in which a rod fits for the purpose of turning the adjusting screw through rotation of the rod.

4. Device as claimed in claim 2, wherein the vertical adjusting screw is enclosed on both sides by telescopically acting tubes.

5. Device as claimed in claim 1, wherein said horizontal adjusting screw has a first outer end and a second outer end, said first outer end co-acting with a threaded passage.

6. Device as claimed in claim 5, wherein the threaded passage is provided in the slide element and the horizontal adjusting screw is provided on its second outer end with a screw head, said coupling piece being provided with a horizontally oriented hole through which the horizontal adjusting screw extends.

7. Device as claimed in claim 5, wherein the threaded passage is provided in said coupling piece, the horizontal adjusting screw being provided on its second outer end with a screw head, and wherein the slide element is provided with a horizontally oriented hole through which the horizontal adjusting screw extends.

8. Device as claimed in claim 1, wherein the dimensions of the guide element and the slide element are closely-sized transversely of the guiding direction.

9. Device as claimed in claim 1, wherein the guide element is a rod mounted between two points of the one shaped part, and the slide element is a hollow tube slidable around this rod.

10. Device as claimed in claim 1, wherein the length of the hollow tube is chosen as a function of the desired maximum lateral displacement.

11. Device as claimed in claim 1, wherein the slide element can be snapped onto the guide element.

12. Device as claimed in claim 1, wherein said vertical adjusting screw has a first and second outer end, said first outer end co-acting with a threaded bore provided on the front side of said other shaped part, and said second outer end being integrated with the coupling piece.

13. Device as claimed in claim 1, wherein the vertical adjusting screw is partially built in a shaped part.

14. Device for treating breathing problems, comprising:
a lower shaped part fitting onto the teeth of the lower jaw,
an upper shaped part fitting onto the teeth of the upper jaw, and
at least one adjustable connecting means between the upper and lower shaped part for forward/backward and upward/downward adjustment of the upper shaped part relative to the lower shaped part,
wherein,
one shaped part of said upper and lower shaped parts is provided at the front with a slide mechanism including a slide element which is slidable laterally to a limited extent along a guide element,
said at least one adjustable connection means includes,
a horizontal adjusting screw for forward/backward adjustment of said one shaped part relative to said other shaped part,
a vertical adjusting screw for the upward/downward adjustment of said one shaped part relative to said other shaped part, and
a coupling piece for coupling said horizontal adjusting screw with said vertical adjusting screw,
said horizontal screw having a first outer end and a second outer end, said first outer end being coupled with the sliding element, and said second outer end being coupled with said coupling piece,
said vertical screw having a first and a second outer end, said first outer end being connected with the front of the other shaped part of said upper and lower shaped parts, and said second outer end being connected with the coupling piece.

15. Device for treating breathing problems, comprising:
a lower shaped part fitting onto the teeth of the lower jaw, an upper shaped part fitting onto the teeth of the upper jaw, and at least one adjustable connecting means between the upper and lower shaped part for forward/backward and upward/downward adjustment of the upper shaped part relative to the lower shaped part, wherein, one shaped part of said upper and lower shaped parts is provided at the front with a slide mechanism including a slide element which is slidable laterally to a limited extent along a guide element, said at least one adjustable connection means includes, a horizontal adjusting screw for forward/backward adjustment of said one shaped part relative to said other shaped part, a vertical adjusting screw for the upward/downward adjustment of said one shaped part relative to said other shaped part, and a coupling piece for coupling said horizontal adjusting screw with said vertical adjusting screw, said horizontal screw having a first outer end and a second outer end, said first outer end being coupled with the sliding element, and said second outer end being coupled with said coupling piece, said vertical screw having a first and a second outer end, said first outer end co-acting with a threaded bore provided on the front side of the other shaped part of said upper and lower shaped parts, and said second outer end being connected with the coupling piece, wherein said first outer end is in front of the teeth when said upper and lower shaped parts are placed in the user's mouth.

* * * * *